United States Patent
Dirisio (10) Patent No.: US 10,505,356 B2
(45) Date of Patent: Dec. 10, 2019

(54) CABLE MANAGEMENT WITH RECIPROCATING BRACKET, SEPARATORS, AND FLEXIBLE BARRIER

(71) Applicant: CARESTREAM HEALTH, INC., Rochester, NY (US)

(72) Inventor: Anthony Dirisio, Rochester, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 15/769,471

(22) PCT Filed: Nov. 21, 2016

(86) PCT No.: PCT/US2016/063031
§ 371 (c)(1),
(2) Date: Apr. 19, 2018

(87) PCT Pub. No.: WO2017/091493
PCT Pub. Date: Jun. 1, 2017

(65) Prior Publication Data
US 2018/0316173 A1    Nov. 1, 2018

Related U.S. Application Data

(60) Provisional application No. 62/259,164, filed on Nov. 24, 2015.

(51) Int. Cl.
*H02G 11/00* (2006.01)
*H05K 5/02* (2006.01)
*A61B 6/00* (2006.01)

(52) U.S. Cl.
CPC ........... *H02G 11/00* (2013.01); *H05K 5/0247* (2013.01); *A61B 6/4085* (2013.01); *A61B 6/56* (2013.01)

(58) Field of Classification Search
None
See application file for complete search history.

(56) References Cited

U.S. PATENT DOCUMENTS 3,001,034 A * 9/1961 Aitken ................... H01R 35/02
191/12 R
3,424,855 A * 1/1969 Westerman .......... H02G 3/0487
174/101

(Continued)

FOREIGN PATENT DOCUMENTS

EP    2 871 738    5/2015
FR    2 911 439    7/2008

(Continued)

OTHER PUBLICATIONS

International Search Report for International application No. PCT/US2016/063031, dated Jul. 2, 2017, 3 pages.

*Primary Examiner* — Timothy J Thompson
*Assistant Examiner* — Muhammed Azam (57) ABSTRACT

An apparatus and method for handling cable motion within a machine comprises a housing having openings for routing cables therethrough. A bracket proximate one opening of the housing secures in a stationary position thereto a first segment of the cables while a reciprocating member proximate another opening of the housing secures thereto another segment of the cables. A spacer body within the housing facilitates routing of the cables within the housing by causing the cables to travel around the body. Separators are attached to groups of the cables to maintain a desired separation there-between and dividers are placed between separated groups of cables to prevent excessive friction therebetween.

15 Claims, 5 Drawing Sheets

(56) References Cited

U.S. PATENT DOCUMENTS

| | | | |
|---|---|---|---|
| 3,433,889 A | | 3/1969 | De Vries |
| 3,551,612 A | * | 12/1970 | Guentner ............... F16L 3/015 |
| | | | 174/69 |
| 3,691,871 A | * | 9/1972 | Gladow .................. F16H 7/00 |
| | | | 33/832 |
| 3,752,180 A | * | 8/1973 | Elder ..................... H02G 11/00 |
| | | | 137/355.17 |
| 3,792,189 A | * | 2/1974 | Stengel ................ H02G 3/0437 |
| | | | 174/69 |
| 3,942,031 A | * | 3/1976 | Bahder .................. H02G 11/00 |
| | | | 307/147 |
| 4,001,593 A | * | 1/1977 | Wing .................... A61B 6/4488 |
| | | | 174/69 |
| 4,065,978 A | * | 1/1978 | Meresz ................... A61B 6/56 |
| | | | 74/82 |
| 4,099,061 A | | 7/1978 | Zink et al. |
| 4,114,043 A | * | 9/1978 | Gansfried ............... A61B 6/56 |
| | | | 174/69 |
| 4,146,795 A | * | 3/1979 | Braden ................... A61B 6/56 |
| | | | 378/194 |
| 4,246,482 A | * | 1/1981 | Zupancic ................ A61B 6/56 |
| | | | 191/12.2 R |
| 4,253,027 A | * | 2/1981 | Taylor .................... A61B 6/032 |
| | | | 191/12 C |
| 4,288,292 A | * | 9/1981 | Hardin, Jr. ............... F16L 3/01 |
| | | | 248/68.1 |
| 4,299,662 A | * | 11/1981 | Hardin, Jr. ........... G21C 13/073 |
| | | | 376/206 |
| 4,343,996 A | * | 8/1982 | Kuipers ................ H02G 11/02 |
| | | | 378/4 |
| 4,366,577 A | * | 12/1982 | Brandt ................ A61B 6/4447 |
| | | | 378/194 |
| 4,667,782 A | * | 5/1987 | Toase ..................... E21F 17/06 |
| | | | 191/12 R |
| 4,769,832 A | * | 9/1988 | Louiday ............... A61B 6/4441 |
| | | | 378/193 |
| 4,816,617 A | * | 3/1989 | Valosen .................. A61B 6/56 |
| | | | 174/68.1 |
| 4,988,831 A | * | 1/1991 | Wilson ................. H05K 5/0247 |
| | | | 174/135 |
| 5,038,371 A | * | 8/1991 | Janssen ............... A61B 6/4441 |
| | | | 378/193 |
| 6,930,244 B1 | * | 8/2005 | Nebel ................. B60R 16/0207 |
| | | | 174/486 |
| 8,647,715 B2 | * | 2/2014 | Di Giuseppantonio .................... |
| | | | C03C 17/25 |
| | | | 427/269 |
| 2005/0236528 A1 | * | 10/2005 | Karlinger ............... H02G 11/00 |
| | | | 248/51 |
| 2007/0165786 A1 | * | 7/2007 | Grasser .................... A61B 6/56 |
| | | | 378/194 |
| 2008/0169127 A1 | * | 7/2008 | Takemoto ........... B60R 16/0215 |
| | | | 174/72 A |
| 2010/0067649 A1 | * | 3/2010 | Noordhoek ........... A61B 6/035 |
| | | | 378/15 |
| 2014/0182262 A1 | * | 7/2014 | Komiya .................. F16G 13/16 |
| | | | 59/78.1 |
| 2016/0323793 A1 | * | 11/2016 | Shi ...................... H04W 36/0061 |
| 2017/0006724 A1 | * | 1/2017 | Clair ........................ H02G 3/22 |
| 2018/0316173 A1 | * | 11/2018 | Dirisio .................. H02G 11/00 |

FOREIGN PATENT DOCUMENTS

| | | |
|---|---|---|
| GB | 2 000 738 | 1/1979 |
| JP | 2011-117552 | 6/2011 |
| WO | 2010/150172 | 12/2010 |
| WO | 2013/141714 | 9/2013 |

* cited by examiner

CABLE MANAGEMENT WITH RECIPROCATING BRACKET, SEPARATORS, AND FLEXIBLE BARRIER

CROSS REFERENCE TO RELATED APPLICATIONS

This application claims the benefit of and is a U.S. National Phase filing of PCT Application PCT/US2016/063031 filed Nov. 21, 2016 entitled "CABLE SYSTEM AND METHOD", in the name of Anthony Dirisio, which claims benefit of U.S. Provisional application U.S. Ser. No. 62/259,164, provisionally filed on Nov. 24, 2015, entitled "CABLE SYSTEM", in the name of Anthony Diriso, all of which are incorporated herein in their entirety.

BACKGROUND OF THE INVENTION

The subject matter disclosed herein is directed to providing electrical power and signal cables to moving machines. In particular, the present patent application discloses apparatus and methods to prevent mechanical problems related to mechanically repeating, reciprocating, alternating, or constant motion of electrical power and signal carrying cables.

BRIEF DESCRIPTION OF THE INVENTION

An apparatus and method for handling cable motion within a machine comprises a housing having openings for routing cables therethrough. A bracket proximate one opening of the housing secures in a stationary position thereto a first segment of the cables while a reciprocating member proximate another opening of the housing secures thereto another segment of the cables. A floating spacer within the housing facilitates routing of the cables within the housing by causing the cables to travel around the spacer. Separators are attached to groups of the cables to maintain a desired separation therebetween and dividers are placed between separated groups of cables to prevent excessive friction therebetween. An advantage that may be realized in the practice of some disclosed embodiments of the cable system and method is for use in cone beam computed tomography applications, such as in the extremity imager identified above and incorporated herein by reference.

In one embodiment, an apparatus and method for handling cable motion within a machine comprises a housing having openings for routing cables therethrough. A bracket proximate one opening of the housing secures in a stationary position a first segment of the cables while a reciprocating member proximate another opening of the housing secures another segment of the cables. A floating spacer within the housing facilitates routing of the cables within the housing by causing the cables to travel around the spacer. Separators are attached to one or more of the cables to maintain a desired separation for the cables. Dividers may be placed between cables to prevent excessive friction therebetween.

In one embodiment, a system for controlling a looping cabled junction from a base connection to reciprocating device connection is disclosed. A reciprocating device travels from a first position to a second position and back again repeatedly while the cables are controlled by structures affixed to at least one cable wherein the structures and cables are maintained in a dynamically controlled spatial relationship between the base connection and the reciprocating device connection. A bendable object that is affixed to both the base connection and the reciprocating device connection controls the location of at least one of the structures.

In another embodiment, an apparatus includes a housing for sets of cables entering the housing at an opening and extending within the housing. The cables exit the housing through a longitudinal slot in the housing. The cables are affixed to a reciprocating device outside the housing that travels back and forth proximate to the slot and in a direction substantially parallel thereto. Separators within the housing are attached to the sets of cables to maintain a separation therebetween.

In another embodiment, a housing with openings includes a plurality of cables passing into the housing through the openings. A reciprocating member proximate one of the openings is attached to the cables. A floating body is positioned in the housing between the cables to prevent the cables from passing over the floating body while they move. A bracket may be used to secure in a stationary position a segment of each of the cables.

In another embodiment, a method includes providing a plurality of cables, affixing a first segment of the cables to a bracket to hold the segment of the cables in a stationary position. A second segment of the cables is affixed to a reciprocating member. One or more of the cables are positioned to diverge around a first side of a spacer. One or more separators are each attached to one or more of the cables to maintain a desired separation. The reciprocating member is driven to travel back and forth between a first position and a second position. One or more of the cables may be positioned to diverge around a second side of the spacer. An elongated divider may be positioned between cables to prevent excessive friction therebetween, and one end of the divider may be attached to the bracket and the other end to the reciprocating member.

In one embodiment, a system for controlling one or more cables is disclosed. The cables are connected to a base and to a reciprocating bracket. A reciprocating device is attached to the reciprocating bracket to move the reciprocating bracket from a first position to a second position one or more times. The cables are passed through a plurality of separators with openings therethrough. The one or more cables are affixed to the separators for the separators to maintain a spatial orientation of the cables. One or more elongated flexible barriers on at least one side of the separators and cables are attached to the base and to the reciprocating bracket.

In one embodiment, an apparatus having a housing includes a first set of cables affixed to a base at an opening of the housing. The cables enter the housing through the opening and extend within the housing in a first direction. A second set of cables affixed to the base at the opening of the housing also enter the housing through the opening and extend within the housing in a second direction transverse to the first direction. The first and the second sets of cables exit the housing through a longitudinal slot. The sets of cables converge toward, and are affixed to, a reciprocating bracket at the longitudinal slot. The reciprocating bracket travels back and forth along the slot. Barriers within the housing are placed adjacent the first set of cables to maintain a first spatial separation therebetween and adjacent the second set of cables to maintain a second spatial separation therebetween.

In one embodiment, an apparatus with a housing having first and second openings includes a plurality of cables. A bracket is positioned proximate one opening to secure in a stationary position a first segment of each of the cables. A reciprocating member proximate another opening has secured thereto a second segment of each of the cables. A spacer is placed within the housing to prevent free movement of the cables during reciprocation. A separator may be attached to a first subset of cables to maintain a first separation between them. Another separator may be attached to another subset of the cables to maintain another separation between each of those cables. Dividers may be placed within the housing, wherein the dividers diverge around the spacer between the cables and the spacer. Additional dividers within the housing may be placed between cables in the first subset of cables and between cables in another subset of the cables. The dividers may be affixed at one end at the bracket and affixed at another end to the reciprocating member which travels back and forth proximate the other opening.

In one embodiment, a method includes providing a plurality of cables and affixing a first segment of each of the cables to a stationary bracket. A second segment of each of the cables is affixed to a reciprocating bracket. A portion of the cables may be extended around a first side of a spacer, and another portion of the cables around another side of the spacer. A separator may be attached to the portion of cables to maintain a separation between them. Another separator may be attached to the other portion of cables to maintain another separation between the other portion of cables. The reciprocating bracket can be driven to travel back and forth between a first position and a second position repeatedly.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale or precise relative shape, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which.

DETAILED DESCRIPTION OF THE INVENTION

This application claims priority to U.S. Patent Application Ser. No. 62/259,164, filed Nov. 24, 2015, in the name of Dirisio, et al., and entitled CABLE SYSTEM.

This application is related in certain respects to U.S. patent application Ser. No. 14/048,599, filed Oct. 8, 2013, in the name of Litzenberger et al., and entitled EXTREMITY IMAGING APPARATUS FOR CONE BEAM COMPUTED TOMOGRAPHY, which is incorporated herein by reference in its entirety.

Figure 1:
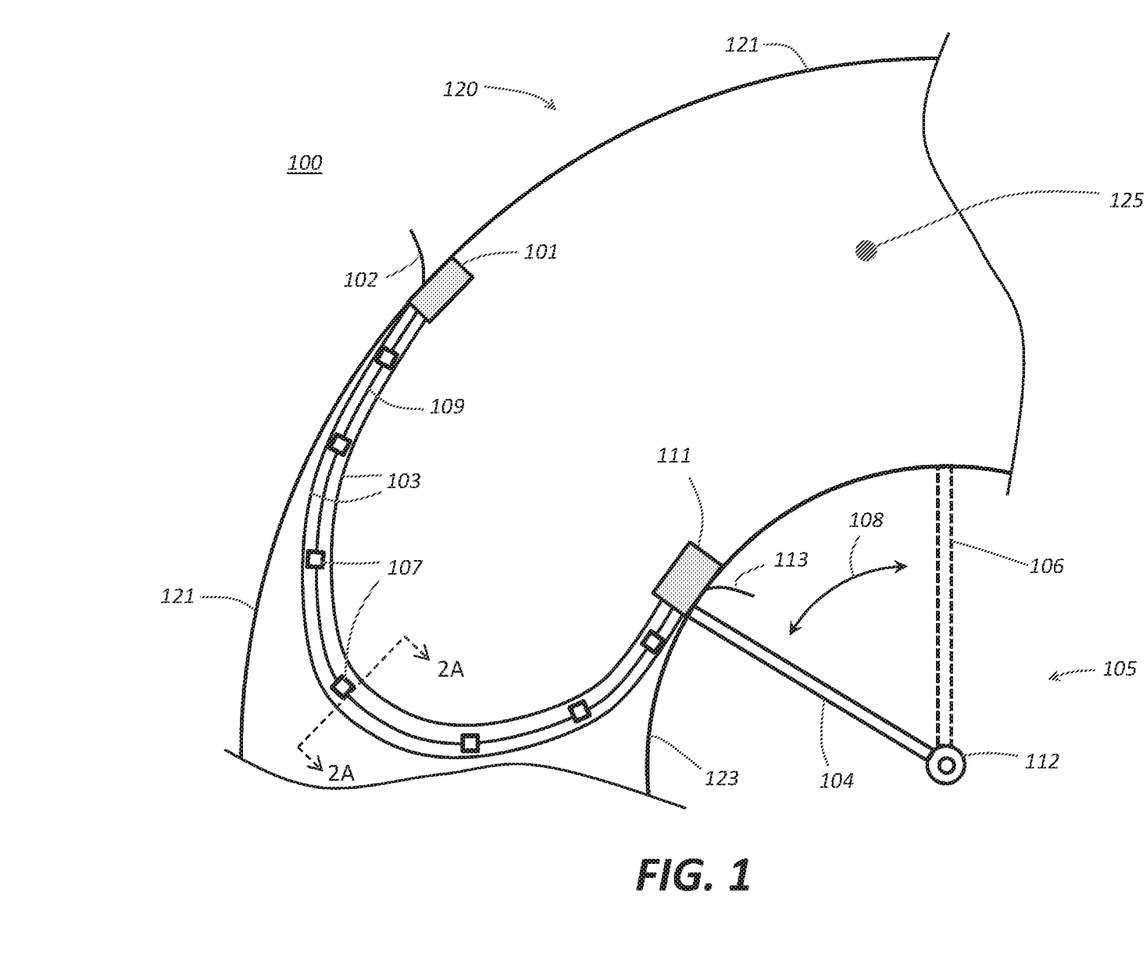
FIG. 1 is a schematic top view cross section diagram of an exemplary cabling system.

FIG. 1 illustrates one embodiment of an inventive cabling system and method for controlling a cable junction. A cable junction may be understood as a location or area wherein incoming electrical power or digital data is received at an apparatus or system that requires electrical power or digital data for its operation. Although the descriptions herein may refer to electrically conductive flexible cables having an insulating cover or sheath, the invention may not be so limited. Other cabling systems, such as flexible optical fiber cable systems, may take advantage of the inventive embodiments disclosed herein. The term cable may refer to a single or multiple flexible conductors (or fibers for data) for transmitting power and/or data thereon, such as if multiple conductors are bundled together physically or are necessary as a multiple bundle to provide proper operation for the receiving apparatus or system.

Referring to the top view provided in FIG. 1, a portion of an apparatus or system 100 requiring electrical power and/or digital data includes a generally circular housing 120 having an exterior, generally circular, side 121 and an interior, generally circular side 123. The exterior and interior sides 121, 123, form portions of the housing 120 which enclose an interior region of the housing 120 between the exterior and interior sides 121, 123. In one embodiment, the power/data receiving apparatus 100 may represent the generally circular housing portion of the cone beam imaging system described in U.S. patent application Ser. No. 14/048,599, identified above and incorporated by reference herein. The electrical and/or data cable includes a portion 102 outside the housing 120 which may be connected to an electrical power supply, or to a data transceiver for transmitting data to and receiving data from the system 100, such as programming data, control data, image correction data, command data, and captured image data, or the like.

The cable 102 passes through a stationary base connector, or bracket, 101 which is shown in a position in the interior 125 of the housing 120, but may be attached to an outside surface of the housing 120. The housing 120 may have an opening therethrough and the bracket 101 may be fixed in the opening. The cable 109 then passes into the interior 125 of the housing 120, and eventually exits the housing 120 through a movable bracket 111 which may be mounted in a curved housing slot (not shown) along the interior side 123 of the housing 120. The bracket 111 is shown in a position in the interior 125 of the housing 120 along the housing side 123, but may be attached outside the housing 120 along the interior housing side 123. The cable 113 exits the housing 120 through movable bracket 111 and may be electrically (or optically) connected to appropriate receiving circuits in the apparatus or system 100. As described herein, a single or stacked cable is identified for convenience as having a portion 102 outside the housing 120, a portion 109 inside the housing 120, and a portion 113 outside the housing 120 through bracket 111 at a location different than the bracket 102. Thus, the incoming portion 102 and the exiting portion 113 refer to the same continuous conductive cable 109.

Figure 2A:
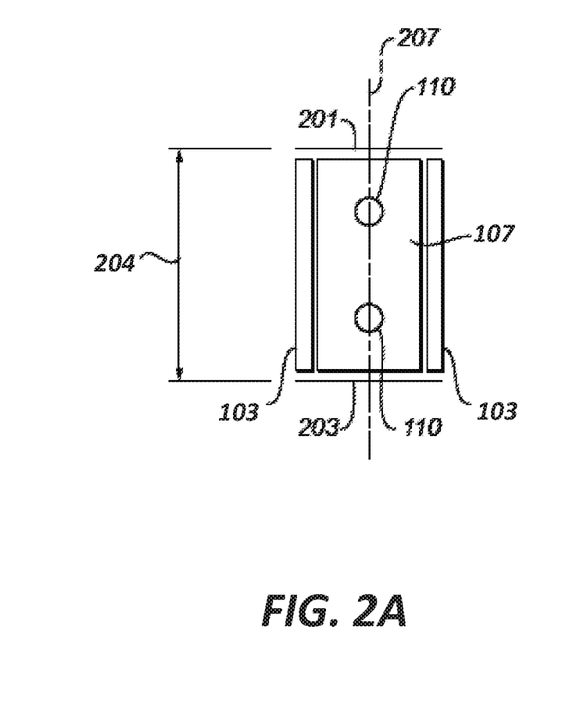
FIG. 2A is schematic front view cross section diagram of a portion of the exemplary cabling system of FIG. 1.
Figure 2B:
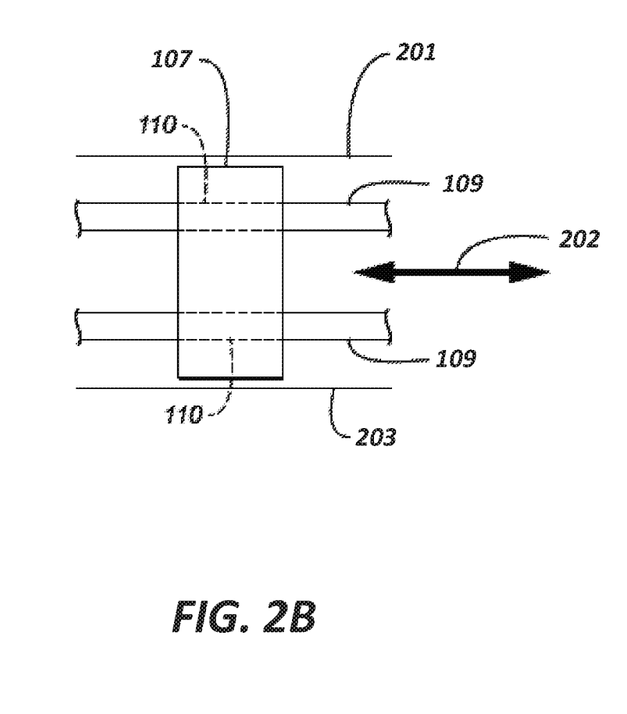
FIG. 2B is a side view of FIG. 2A.

The single or multiple stacked (FIG. 2) cable 109, which may carry incoming electrical power and/or digital data, is secured at one portion to a stationary base connection, or bracket 101, to prevent sliding movement of the cable 109 through the bracket 101 even though the cable 109 passes through openings in the bracket 101 to enter the housing 120. The cable 109 may be a power cable supplying voltage and current or it may be a communication cable for transmitting data, or a combination thereof. The cable 109 is secured, at another portion of the cable, to a movable bracket 111 which moves in a reciprocating or alternating fashion, as indicated by the arrow 108, from a first position 104 to a second position 106, and back again, repeatedly. The cable 109 passes through openings in the bracket 111, but the cable 109 is secured at one portion to the movable bracket 111 to prevent sliding movement of the cable 109 through the bracket 111. Although the first and second positions 104, 106, are shown separated by an angle of about 60°, the first and second positions may be separated by less than 60°, such as about 10°, or the first and second positions may be separated by an angle greater than 180° such as about 230°.

The bracket 111 and cable 109 are moved in a reciprocating fashion between the first and second positions 104, 106, by rigidly connecting the bracket 111 to an arm 105 that is, in turn, rigidly connected to a motor-driven shaft 112 that is controllably rotated in the reciprocating fashion to drive the arm 105 and thereby the bracket 111 and cable 109 between the first and second positions 104, 106, repeatedly. In one embodiment, the illustrated cable system and method may be considered as a system for controlling a looping cabled junction from the base connection 101 to the reciprocating arm 105. As shown in FIG. 1, the term reciprocating assembly may include the motor-driven shaft 112, the arm 105, and the bracket 111. The bracket 111 travels from the first position 104 to the second position 106, and back, repeatedly, as indicated by the arrow 108, while a segment of the cable 109 is attached to the bracket 111. The arm 105 may be attached to the bracket 111 through a slot along the interior side 123 of the housing 120. The interior side 123 of the housing 120 may be provided with a grooved track to guide the bracket 111 along the tack, as necessary.

A cable assembly to protect the cable 109 from mechanical problems such as abrasion, fatigue, and other mechanical degradations will now be described. Referring to FIG. 1, a plurality of structures 107, which may be referred to herein as separators, are affixed to the cable 109 wherein the plurality of separators 107 maintain a stack (FIG. 2) of cables 109 or a single cable 109 separated from each other and separated from interior surfaces of the housing 120. A flexible strip 103, which may be referred to herein as a barrier, or divider, 103 is shaped in the form of an elongated flat band, placed adjacent to at least one side of the cable 109 and its separators 107. Multiple barriers 103 (as shown in FIG. 1) may be positioned on opposite sides of the cable 109 and its separators 107. The cable 109, together with separators 107 and barriers 103 may be referred to altogether as a cable assembly. As the context of the description herein may require, the brackets 101, 111, may also be included in the term cable assembly. Though flexible, the barriers 103 may be selected from a material having greater stiffness than the cable 109 to serve to push the separators 107, and thereby the cable 109, to maintain the generally curved shape of the cable assembly, as shown in FIG. 1, as the reciprocating assembly reciprocates. The presence and design of the barriers 103 help to prevent completely free motion of the cable 109 during reciprocating movement which may cause unwanted mechanical degradation of the cable and/or its protective insulating layers.

The barrier 103, as a flat elongated band, may also be affixed at one end to the bracket 101 and to the bracket 111 at another end. In one embodiment (not shown) one or two of the separators 107 for the cable 109 may each be affixed at one or both brackets 101, 111. The separators 107 may each include multiple openings threthrough so that they may also be affixed to multiple stacked cables 109, as described herein, wherein each of the cables 109 are stacked such that the center of each of the cables are co-linear along a vertical line 207 (FIG. 2) that is orthogonal to the direction of travel 202 (FIG. 2) of the cable assembly.

As shown in the system of FIG. 1, the cable 102 may enter the housing 120 through an opening in the housing 120 proximate the base, or bracket, 101, which bracket may be affixed to the housing 120 as described herein, and through an opening in the bracket 101. The other end of the cable 113 may exit the housing through a slot proximate the bracket 111. A portion or segment of the cable 109 may be affixed to the bracket 101 and another portion affixed to the bracket 111, such as by using tightened compression brackets having openings through which the cable passes, or a frictional attachment, as desired. As shown in FIG. 1, the long dimension of a slot through which the bracket 111 is attached to arm 105, is parallel to the page and is formed in the interior housing side 123. The configuration of the housing side 123 and its slot may be better understood with reference to FIG. 5 as described herein.

Referring now to FIGS. 2A and 2B, wherein FIG. 2A illustrates a cross section view through the plane of movement of the cable assembly disclosed herein. FIG. 2B is a side view of FIG. 2A. A front view of the separator 107 is illustrated in FIG. 2A, wherein the separator 107 is disposed between an upper surface 201 of the housing 120 and a lower surface 203 of the housing 120, whereby the upper surface 201 of the housing 120 and a lower surface 203 of the housing 120 are separated by a housing depth 204. The height of the separator 107 (parallel to the housing depth 204) is selected to be slightly smaller than the housing depth 204, to avoid excessive friction between the separator 107 and the upper 201 and lower 203 surfaces of the housing, and large enough so that the separator is not able to rotate excessively inside the housing 120, such as in a clockwise or counterclockwise direction in the view of FIG. 2A to deviate from a substantially vertical orientation, during the reciprocating movement of the cable assembly. Thus, the top and bottom surfaces of the separators 107 which face the upper and lower surfaces 201, 203, of the housing 120, respectively, may be generally of a planar shape to be positioned substantially parallel to the upper and lower surfaces 201, 203, of the housing 120. One dimension in the plane of movement of the cable assembly is indicated by the arrow 202.

The separator 107 includes at least one straight-line opening 110 therethrough in a direction substantially parallel to the plane of reciprocating movement of the cable assembly within the housing 120. The cable or cables 109 pass through the openings 110 and are fixed in position by the separators 107, such as by a frictional compressive fitting in the separators 107. The separators 107 may each be formed integrally as a single piece that may require inserting the cables 109 therethrough, or the separators 107 may be formed in two pieces split at the openings 110 and configured to be attached together, such as by being screwed together or clamped together to provide a compression fit about the cables 109. The cable configuration of FIG. 2A illustrates a stacked two cable configuration, however, the separators 107 may include only one cable therethrough, or two or more cables, as shown in FIGS. 2A-2B, arranged collinearly along a vertical line 207 that is substantially perpendicular to the upper and lower surfaces 201, 203 of the housing 120. In one embodiment, the separators 107 may include three or more cables arranged noncollinearly therethrough, such as four cables passing through four openings arranged in the shape of the four corners of a rectangle. Multiple cables arranged to pass simultaneously through common separators 107 may be referred to herein as a group of cables. As will be described in other embodiments of the invention herein, multiple groups of cables may be propelled through the reciprocating movement of the cable assembly disclosed herein. The sizes of the separators may be preferably selected to be of a common size in one cable assembly or in one system 100. In some embodiments, they may be selected to be of different sizes, such as having a common height but a different width or different number of openings therethrough. The cable groups may each include a different number of cables, thus, as between groups of cables, the separators may have a different number of openings therethrough.

FIG. 2B illustrates a side view of FIG. 2A whereby the cables 109 are disposed in the openings, or channels, 110 of the separator 107 and extend therethrough. In one embodiment, a separator 107 having one opening 110 therethrough serves to maintain a separation of the cable 109 between upper and lower surfaces 201, 203, of the housing 120. In one embodiment, a separator 107 having two or more channels 110 therethrough serves to maintain a separation of the cables 109 between each other and between the upper and lower surfaces 201, 203, of the housing 120.

Turning to the barrier, or the elongated flat band, 103, a height of the divider 103 is also slightly less than the housing depth 204 to allow a substantially low friction movement of the divider 103 therein. The divider 103, or dividers if they are disposed on both sides of the cable 109 and separators 107, moves together with the cable 109 and separators 107 during the reciprocating movement of the cable assembly. The dividers 103 are secured at both ends to the brackets 101, 111, and are generally disposed perpendicular to the upper and lower surfaces 201, 203, of the housing 120, but are generally unsecured along their length and may be made from a somewhat flexible material, but rigid enough to maintain a vertical orientation within the housing 120 during the reciprocating movement of the cable assembly, so long as their ends are secured in a vertical orientation to the brackets 101, 111. Thus, the divider 103 may be slightly tilted away from a perpendicular direction at various times by the reciprocating movement of the cable assembly as disclosed herein. Thus, the separators 107 and the barriers 103 allow substantially low-friction movement of the cable assembly within the housing 120 as the reciprocating assembly travels back and forth between alternating positions 104, 106. The material of the separators 107 and the barrier 103 may be selected to provide minimal friction against the upper and lower surfaces 201, 203, of the housing 120.

Figure 3:
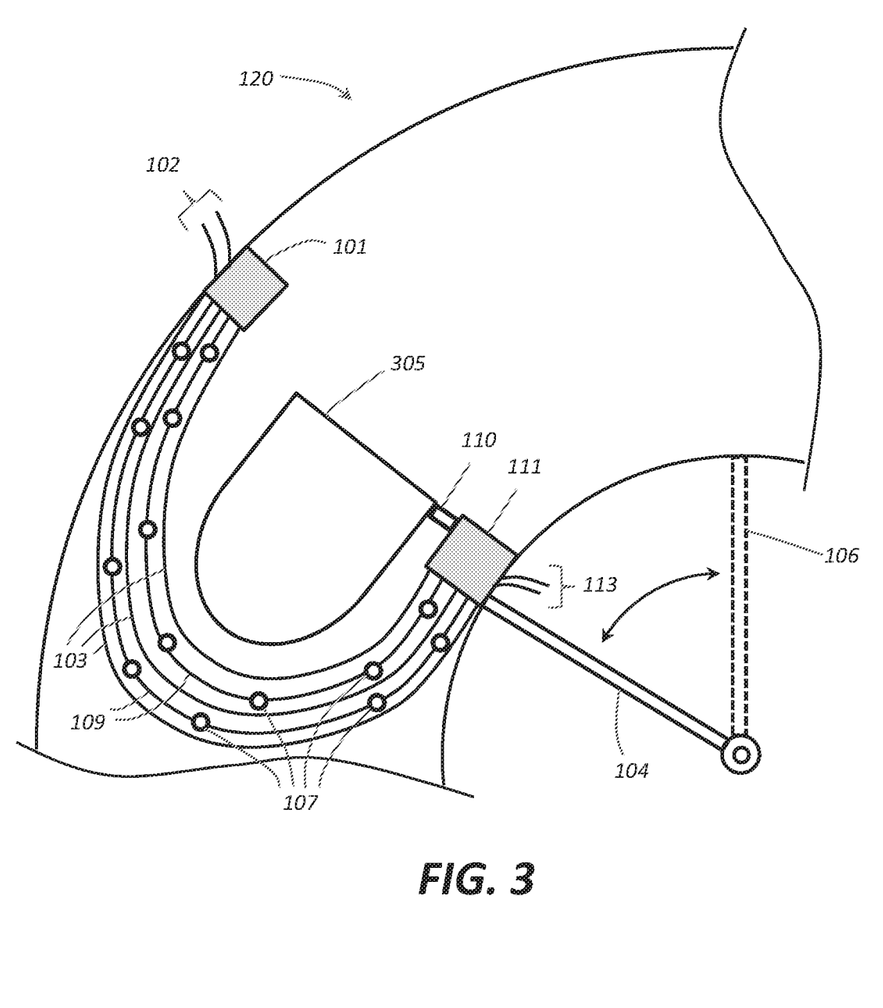
FIG. 3 is a schematic top view cross section diagram of another exemplary embodiment of a cabling system.

FIG. 3 illustrates further embodiments of the inventive cabling system disclosed herein. Some components that are unmodified in relation to FIG. 1, and are already described in relation to FIG. 1, are not enumerated in FIG. 3 for clarity. In the embodiments of FIG. 3, groups of cables 109, e.g. two groups in the embodiment of FIG. 3, are secured to brackets 101, 111, which brackets may be enlarged to accommodate a larger number of cables passing therethrough, but are otherwise similar in structure and function. As before, the cables 109 may be power cables supplying voltage and current or they may be communication cables for transmitting data, or a combination thereof. In one embodiment, one or more groups of cables 109 each pass through a plurality of separators 107 that are each affixed to the cables in a group, wherein the plurality of separators 107 maintain a dynamically controlled space between the cables 109. In an embodiment that includes multiple groups of cables, barriers 103 may be positioned between the cable groups, e.g., three barriers 103 in the embodiment of FIG. 3, whereby each cable group is said to have a barrier 103 on two sides thereof. As described in reference to FIGS. 1-2B, all the barriers 103 may be each affixed in a vertical orientation to both the stationary bracket 101 and the movable, or reciprocating, bracket 111, which movable bracket 111 is attached to the reciprocating arm 105, and the cable groups may also each pass through each of the brackets 101, 111, and be fixed thereto to prevent sliding movement of the cables through the brackets 101, 111. The barriers 103 placed between the cable groups control the location of the separators 107 by maintaining a spatial separation therebetween and, thereby, between the cables 109. As described herein, the separators 107 may be configured to secure the cables 109 in a stacked configuration such that the center of each of the cables are co-linear along a line 207 orthogonal to the direction of travel of the cable assemblies and to the upper and lower housing surface 201, 203, of the housing 120. As shown in FIG. 3, the separators 107 may have a circular cross-section as seen in the top view of FIG. 3, or they may have a rectangular cross-section as seen in FIG. 1. FIGS. 2A-2B, and their description above, apply equally to the circular embodiment of the spacers 107.

The cabling system of FIG. 3 further illustrates use of a spacer 305. The spacer 305, in one embodiment, may be connected to the reciprocating bracket 111 using a rigid connector 110. In another embodiment, described herein, the spacer may be unsecured and in free play, e.g., as a free floating body, to move about an interior of the housing 120 as urged by contact with the cables 109, contact with the separators 107, or by contact with the barrier, or divider, 103. Similarly, movement of a barrier 103 may be limited to a certain extent by the spacer 305. In one embodiment, the spacer 305 may serve to push the cable assembly within the housing 120, as shown in FIG. 3, as the reciprocating assembly moves from the second position 106 back to the first position 104.

Figure 4:
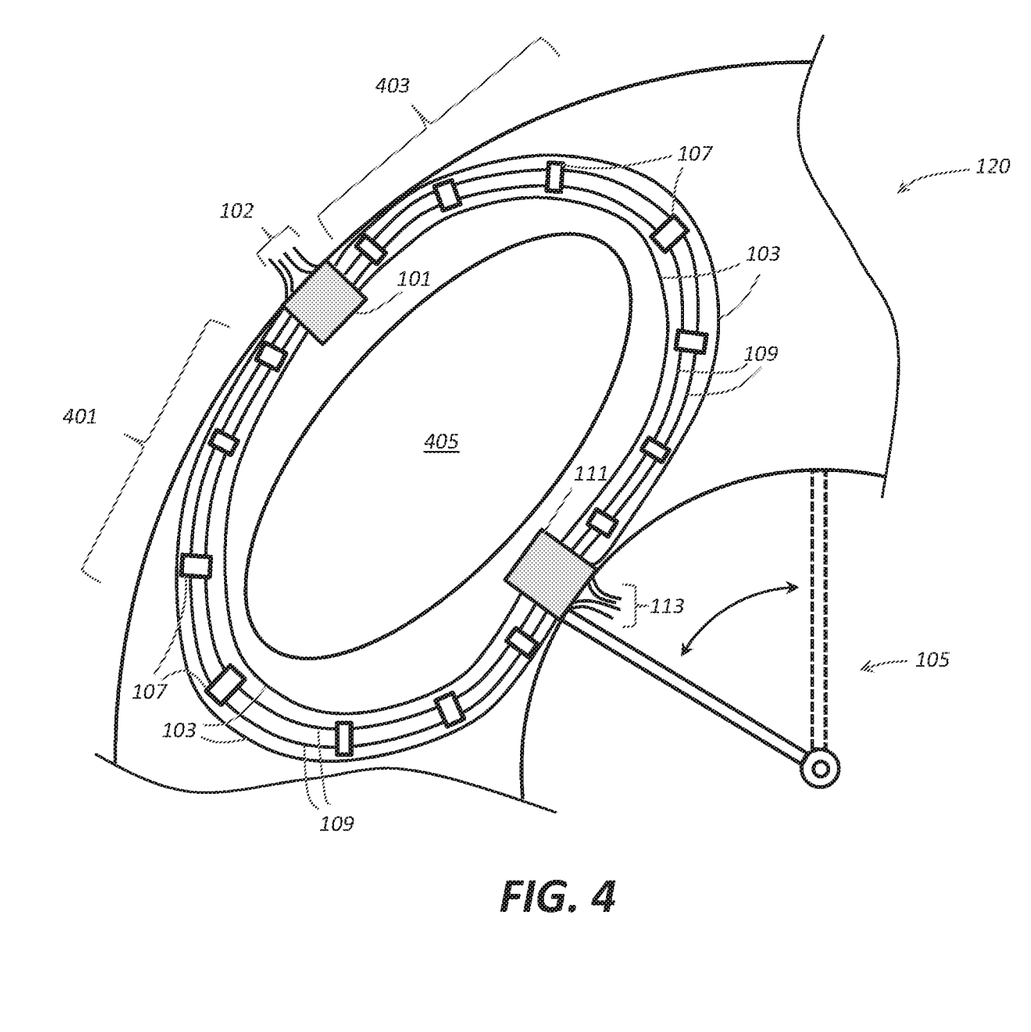
FIG. 4 is a schematic top view cross section diagram of another exemplary embodiment of a cabling system.

FIG. 4 illustrates an embodiment of a cabling system that operates in a fashion as described herein with respect to the embodiments of FIGS. 1 and 3, and which will not be repeated herein. The cabling system of FIG. 4 illustrates a plurality of separators 107, cables 109, and dividers 103 disposed in opposable loops 401, 403, about a floating body 405. That is, the incoming cables 102 outside the housing 120 enter the housing 120 at a stationary bracket 101 and diverge around a floating spacer 405, i.e., a first portion, or loop, 401 of the cables 109 extends around a first side of the floating body 405, while a second portion, or loop, 403 of the cables 109 extends around a second, or opposite, side of the floating body 405. The cables 109 then converge at the reciprocating bracket 111. The cables 113 exit the housing 120 at the reciprocating bracket 111. The diverging cable portions 401, 403, each also include the separators 107 and barriers 103, i.e., diverging cable assemblies. The separators 107 may include sufficient openings to separate two stacked parallel columns of cables, e.g., four or more cables passing through each separator 107, as described in an alternative embodiment of the separators shown in FIGS. 2A-2B. A first one of the cable loops 401, 403, may include power cables and a second one of the loops, 401, 403, may include data cables. In one embodiment, the illustrated system may be considered as a system for controlling a looping cabled junction from the base connection 101 to the reciprocating device 105 connection. The reciprocating device 105 may travel back and forth from a first position to a second position, as described herein with reference to FIG. 1. In one embodiment, a plurality of separators 107 are each affixed to two or more cables 109 wherein the plurality of separators 107 and the cables 109 maintain a dynamically controlled space therebetween as well as between the base connection 101 and the connection at the reciprocating device 105.

The system of FIG. 4 may include a housing 120 whereby the cables 109 may pass into the housing 120 through an opening therein proximate the base 101. The cables 109 may pass out of the housing 120 through another opening, or slot, and be attached to the reciprocating device 105. The cabling system embodiment of FIG. 4 illustrates use of a spacer in a floating body 405 embodiment, which floating body may be unsecured and free to move about an interior of the housing 120 as urged by contact with the cables 109, contact with the separators 107, or by contact with the dividers 103. As illustrated in FIG. 4, the cables 109 may diverge and extend around the floating body 405 to be secured to reciprocating device 105. The floating body 405 serves, in this embodiment, to maintain a separation between diverging subsets of the cables 109. In one embodiment, the cables 109 which serve as power transmission cables may diverge in one direction around the floating body 405 while a second subset of the cables 109 which serve as data transmission cables diverge in another opposite direction around the floating body 405. The cabling system of FIG. 4 may utilize the housing 120 whereby the cables 102 may enter the housing120 through an opening therein proximate the bracket 101, and whereby the cables 113 may exit the housing 120 through a slot proximate the reciprocating device 105, and may be attached to the reciprocating device 105. As shown in FIG. 4, the long dimension of such a slot is parallel to the page and is formed in a side of the housing 120 as described with reference to FIG. 1 and which may be better understood with reference to the description of FIG. 5. The reciprocating device 105 reciprocates in a direction parallel to the long dimension of the slot and is substantially parallel to a curve of the housing 120 as shown in FIG. 4.

Figure 5:
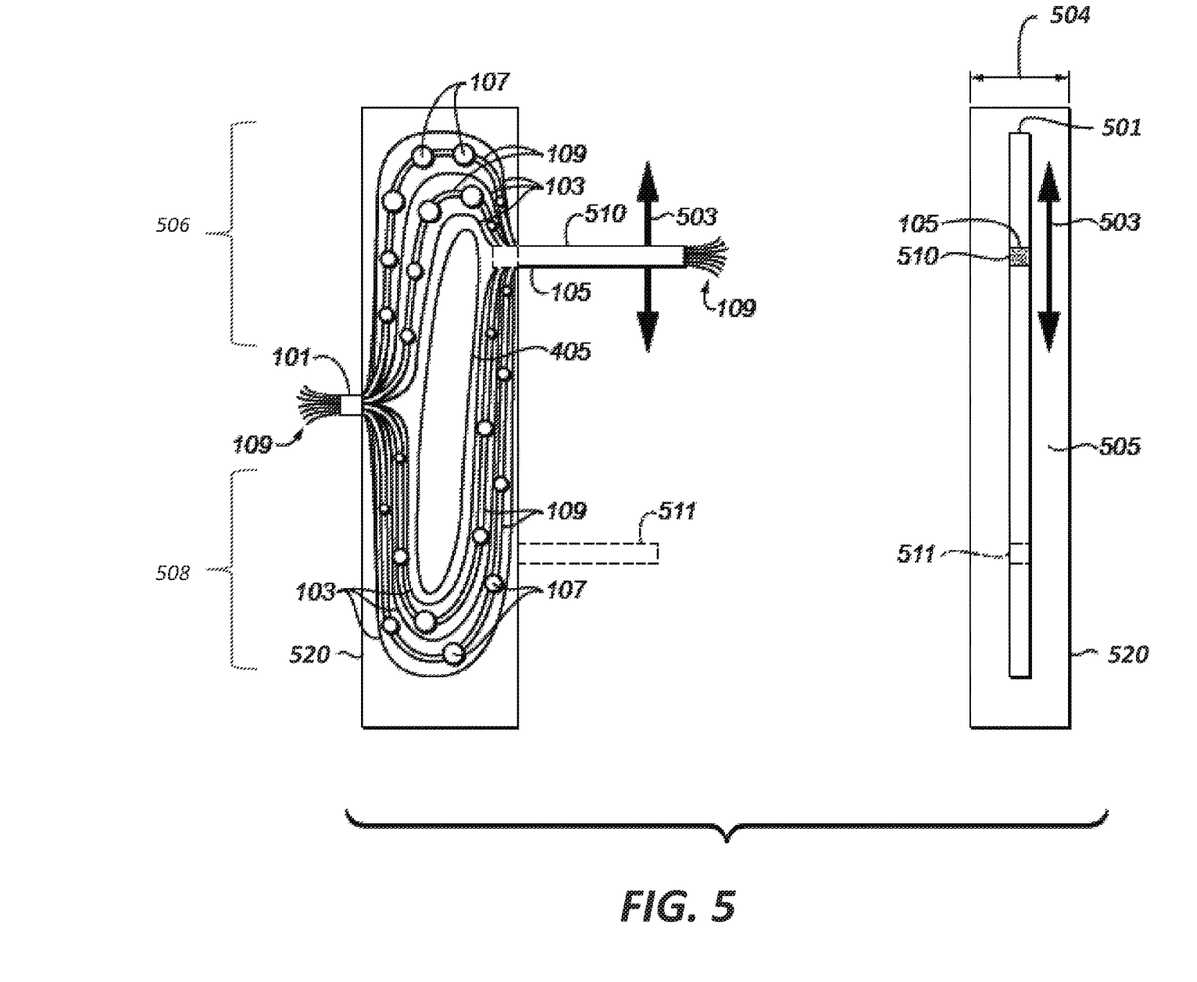
FIG. 5 is a schematic cross section diagram of another exemplary embodiment of a cabling system.

FIG. 5 illustrates a front cross-section and side views of a linear cabling system embodiment, similar in many respects to the cabling system structures of FIGS. 1-4, for controlling a cable junction. A substantially rectangular shaped housing 520 may be considered to enclose a first set of cables 109 affixed to a stationary bracket 101 at an opening (not shown) of the housing 520, wherein a first set 506 of cables 109 enter the housing 520 through the opening and extend within the housing 520 and diverge around floating body 405, eventually reaching the reciprocating member 105 and may be attached thereto to prevent sliding movement of the cables 109 through the reciprocating member 105. In the embodiment of FIG. 5, the reciprocating member 105 travels in a reciprocating fashion as indicated by the arrow 503 back and forth linearly and parallel to a linear slot 501 in a side of the housing 520. The reciprocating member 105 may travel back and forth linearly between positions 510 and 511, for example. A second set 508 of data cables 109 may also be affixed to the stationary bracket 101 at the opening of the housing 520 and enter the housing 520 through the opening and extend within the housing 520 to diverge from the first set 506 of cables 109 around an opposite side of the floating body 405. The second set 508 of cables 109 may also be attached to the reciprocating member 105. The first and second sets 506, 508 of cables 109 may converge and exit the housing 520 through the reciprocating member 105 at a longitudinal slot 501 in one side of the housing. The first set and the second sets 506, 508, of cables 109 may be affixed to the reciprocating device 105 which extends outside the housing 520. The reciprocating device may travel back and forth as shown by arrow 503 proximate to the slot and in a direction substantially parallel thereto. The power and data cables 109 may be separately routed in opposite directions around the floating body 405 within the housing. The cables 109 may be power cables supplying voltage and current or they may be communication cables for transmitting data, or a combination thereof. The reciprocating device 105 may travel from a first position 510 to a second position 511 as indicated by the arrows 503. As described herein, a plurality of separators 107, are affixed to two or more cables 109 wherein the plurality of separators 107 and the cables 109 maintain a dynamically controlled space between the bracket 101 and the reciprocating device 105. The divider 103 may be positioned adjacent the cables and may be affixed to both the bracket 101 and the reciprocating device 105 to control movement of at least one of the separators 107 and its attached cables. The separators 107 may also be affixed to multiple cables 109 as described herein, wherein each of the cables 109 are stacked such that the center of each of the cables are co-linear along a line 207 and are orthogonal to the top and bottom surfaces of the housing 520. As shown in FIG. 5, the slot 501 is formed in one of the housing sides 505. The reciprocating device 105 reciprocates proximate to the slot 501 between positions 510, 511, proximate to ends of the slot 501 in a direction parallel to the long dimension of the slot 501 as indicated by arrow 503.

The plurality of dividers 103 may be disposed between and adjacent to the power cables on one side of the floating body 405, and between the data cables 109 on an opposite side of the floating body 405. As described herein, the housing 520 comprises a depth dimension 504 measured between major substantially parallel surfaces of the housing 520. The separators 107 and the dividers 103 comprise a dimension slightly less than the depth dimension to allow free movement thereof within the housing 520. The floating body 405 also comprises a depth (thickness) less than the depth dimension 504 to allow free movement thereof within the housing and is disposed between the first set of cables 109 and the second set of cables 109 to maintain a separation therebetween.

The dividers 103 may be free floating or one or two may be affixed at one end at the bracket 101 and affixed at a second end to the reciprocating device 105. To enable electrical power and data transmission, the cables 109 each comprise one or more conductors as well as a protective insulating sheath.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A system for controlling movement of cables connected to a base and to a reciprocating bracket, the system comprising:
a housing having a horizontal upper interior surface and a horizontal lower interior surface substantially parallel to the horizontal upper interior surface, the horizontal upper interior surface separated from the horizontal lower interior surface by a first distance;
a reciprocating device attached to the reciprocating bracket to move the reciprocating bracket from a first position to a second position;
a plurality of separators each having vertically aligned openings therethrough, the plurality of separators each further having a substantially flat top surface and a substantially flat bottom surface for contacting the horizontal upper interior surface of the housing and the horizontal lower interior surface of the housing, respectively, to prevent an angular displacement of the plurality of separators from a vertical alignment, the plurality of separators each having a height between the top surface and the bottom surface less than the first distance, the cables passing through the vertically aligned openings and affixed to the plurality of separators, the plurality of separators for maintaining the cables vertically aligned at the plurality of separators; and
an elongated flexible barrier on at least one side of the plurality of separators and the cables, the elongated flexible barrier comprising a first end attached to the base and a second end attached to the reciprocating bracket.

2. The system of claim 1, wherein the cables are oriented such that a center of each of the cables are co-linear along a direction orthogonal to the horizontal upper interior surface and the horizontal lower interior surface.

3. The system of claim 1, further comprising a floating body between the cables to maintain a spatial separation between the cables.

4. The system of claim 3, wherein the floating body is rigidly connected to the reciprocating device.

5. The system of claim 1, wherein a first one of the cables comprises a power cable and a second one of the cables comprises a data cable.

6. An apparatus comprising:
a housing comprising a horizontal upper surface and a horizontal lower surface substantially parallel to the horizontal upper surface;
a first set of cables affixed to a base at an opening of the housing, the first set of cables entering the housing through the opening and extending within the housing in a first direction;
a second set of cables affixed to the base at the opening of the housing, the second set of cables entering the housing through the opening and extending within the housing in a second direction transverse to the first direction;
the first set and the second set of cables exiting the housing through a longitudinal slot in the housing, the first set and the second set of cables converging toward, and affixed to, a reciprocating bracket at the longitudinal slot, the reciprocating bracket configured to travel back and forth along the longitudinal slot and in a direction substantially parallel thereto;
one or more first barriers within the housing adjacent the first set of cables to maintain a first spatial separation therebetween;
separators disposed between the horizontal upper interior surface and the horizontal lower interior surface, the separators affixed to each of the first and the second set of cables, the separators having generally planar top and bottom surfaces and a height less than a distance between the horizontal upper surface and the horizontal lower surface of the housing to prevent the separators from rotating excessively within the housing and to maintain central axes of each of the first and the second set of cables in a vertical linear orientation at the separators perpendicular to the horizontal upper surface and the horizontal lower surface of the housing; and
one or more second barriers within the housing adjacent the second set of cables to maintain a second spatial separation therebetween.

7. An apparatus comprising:
a housing having a first opening in a first side of the housing, a second opening in a second side of the housing, a horizontal upper interior surface and a horizontal lower interior surface parallel to the horizontal upper interior surface;
a plurality of cables;
a bracket proximate the first opening to secure in a stationary position a first segment of each of the plurality of cables;
a reciprocating member proximate the second opening and having secured thereto a second segment of each of the plurality of cables;
separators disposed between the horizontal upper interior surface and the horizontal lower interior surface, the separators affixed to the plurality of cables, the separators having generally planar top and bottom surfaces and a height less than a distance between the horizontal upper interior surface and the horizontal lower interior surface of the housing to prevent the separators from rotating excessively within the housing and to maintain central axes of the plurality of cables in a vertical linear orientation at the separators perpendicular to the horizontal upper interior surface and the horizontal lower interior surface of the housing; and
a spacer within the housing,
wherein the plurality of cables extend through the first opening into the housing, extend around one side of the spacer, and extend through the second opening out of the housing.

8. The apparatus of claim 6, wherein at least one of the one or more first barriers is disposed between cables in the first set of cables, and wherein at least one of the one or more second barriers is disposed between cables in the second set of cables.

9. The apparatus of claim 6, wherein the housing is curved, and wherein a reciprocating device travels back and forth along a curved longitudinal slot.

10. The apparatus of claim 6, wherein the housing is substantially rectangular, and wherein a reciprocating device travels back and forth along a linear longitudinal slot.

11. The apparatus of claim 6, wherein the separators and the one or more first barriers and the one or more second barriers comprise a height dimension slightly less than a distance between the horizontal upper and lower surfaces of the housing.

12. The apparatus of claim 6, further comprising a floating body within the housing, the floating body disposed between the first set of cables and the second set of cables to maintain a spatial separation therebetween.

13. The apparatus of claim 6, wherein the one or more first barriers and the one or more second barriers each comprise a first end affixed to the base, and wherein the one or more first barriers and the one or more second barriers each comprise a second end affixed to the reciprocating bracket.

14. The apparatus of claim 6, wherein the first set of cables each comprise a conductor for power transmission, and wherein the second set of cables each comprise a conductor for data transmission.

15. The apparatus of claim 7, wherein a first subset of the plurality of cables and a second subset of the plurality of cables diverge within the housing, the first subset of the plurality of cables extend around a first side of the spacer within the housing, and wherein the second subset of the plurality of cables diverge around a second side of the spacer within the housing.

\* \* \* \* \*